(12) United States Patent
Avendi et al.

(10) Patent No.: US 11,766,234 B2
(45) Date of Patent: Sep. 26, 2023

(54) SYSTEM AND METHOD FOR IDENTIFYING AND NAVIGATING ANATOMICAL OBJECTS USING DEEP LEARNING NETWORKS

(71) Applicant: Avent, Inc., Alpharetta, GA (US)

(72) Inventors: Michael R. Avendi, Irvine, CA (US); Shane A. Duffy, Irvine, CA (US)

(73) Assignee: Avent, Inc., Alpharetta, GA (US)

( * ) Notice: Subject to any disclaimer, the term of this patent is extended or adjusted under 35 U.S.C. 154(b) by 371 days.

(21) Appl. No.: 16/618,836

(22) PCT Filed: May 17, 2018

(86) PCT No.: PCT/US2018/033117
§ 371 (c)(1),
(2) Date: Dec. 3, 2019

(87) PCT Pub. No.: WO2018/226377
PCT Pub. Date: Dec. 13, 2018

(65) Prior Publication Data
US 2020/0138406 A1    May 7, 2020

Related U.S. Application Data

(60) Provisional application No. 62/515,716, filed on Jun. 6, 2017.

(51) Int. Cl.
*A61B 8/00*    (2006.01)
*A61B 8/08*    (2006.01)
(Continued)

(52) U.S. Cl.
CPC ............ *A61B 8/085* (2013.01); *A61B 8/4254* (2013.01); *A61B 8/461* (2013.01); *A61B 8/5207* (2013.01);
(Continued)

(58) Field of Classification Search
CPC ..... A61B 8/4254; A61B 8/461; A61B 8/5207; A61B 8/5223; G06F 3/016; G06N 3/08;
(Continued)

(56) References Cited

U.S. PATENT DOCUMENTS 5,906,578 A    5/1999  Ratan et al.
11,096,663 B2    8/2021  Schneider et al.
(Continued)

FOREIGN PATENT DOCUMENTS

EP    2 567 660 A2    3/2013
WO    WO 2016/134916 A1    9/2016
WO    WO 2017/222970 A1    12/2017

OTHER PUBLICATIONS

Baby et al., "Automatic Nerve Segmentation of Ultrasound Images", 2017 International Conference of Electronics, Communication and Aerospace Technology (ICECA), vol. 1, Apr. 20, 2017, pp. 107-112.
(Continued)

*Primary Examiner* — Serkan Akar
*Assistant Examiner* — Amal Aly Farag
(74) *Attorney, Agent, or Firm* — Dority & Manning, P.A.

(57) ABSTRACT

A method for scanning, identifying, and navigating at least one anatomical object of a patient via an imaging system. Such system includes scanning the anatomical object via a probe of the imaging system, identifying the anatomical object via the probe, and navigating the anatomical object via the probe. Further, the method includes collecting data, inputting the collected data into a deep learning network configured to learn the scanning, identifying, and navigating steps. In addition, the method includes generating a probe visualization guide for an operator based on the deep learning network. Thus, the method also includes displaying the probe visualization guide to the operator wherein the probe visualization guide instructs the operator how to maneuver
(Continued)

the probe so as to locate the anatomical object. In addition, the method also includes using haptic feedback in the probe to guide the operator to the anatomical object of the patient.

14 Claims, 4 Drawing Sheets

(51) Int. Cl.
| | | |
|---|---|---|
| G06F 3/01 | (2006.01) | |
| G06N 20/00 | (2019.01) | |
| G06N 3/08 | (2023.01) | |
| G06V 10/764 | (2022.01) | |
| G06V 10/82 | (2022.01) | |
| G06V 10/44 | (2022.01) | |

(52) U.S. Cl.
CPC ............... *G06F 3/016* (2013.01); *G06N 3/08* (2013.01); *G06N 20/00* (2019.01); *G06V 10/764* (2022.01); *G06V 10/82* (2022.01); *G06V 10/454* (2022.01)

(58) Field of Classification Search
CPC ...... G06N 20/00; G06K 9/6274; G06V 10/82; G16H 30/20; G16H 30/40
See application file for complete search history.

(56) References Cited

U.S. PATENT DOCUMENTS

| | | | |
|---|---|---|---|
| 2015/0065803 A1 | 3/2015 | Douglas et al. | |
| 2016/0035093 A1* | 2/2016 | Kateb ................ | G02B 21/0012 382/131 |
| 2016/0157831 A1 | 6/2016 | Kang et al. | |
| 2016/0324501 A1* | 11/2016 | Vignon ................ | A61B 8/0841 |
| 2017/0181726 A1 | 6/2017 | Schneider et al. | |
| 2017/0262982 A1* | 9/2017 | Pagoulatos .............. | A61B 8/46 |

OTHER PUBLICATIONS

International Search Report and Written Opinion for PCT/US2018/033117, dated Oct. 2, 2018, 13 pages.
Dai et al., "Instance-aware Semantic Segmentation via Multi-task Network Cascades", 2016 IEEE Conference on Computer Vision and Pattern Recognition, Jun. 27, 2016, pp. 3150-3158.
Hoey et al., "Semi-supervised learning of a POMDP model of Patient-Caregiver Interactions", IJCAI Workshop on Modeling Others from Observations, Jul. 30, 2005, 9 pages.
Hong et al., "Decoupled Deep Neural Network for Semi-supervised Semantic Segmentation", Advances in Neural Information Processing Systems 28, Dec. 7, 2015, pp. 1-9.

* cited by examiner

SYSTEM AND METHOD FOR IDENTIFYING AND NAVIGATING ANATOMICAL OBJECTS USING DEEP LEARNING NETWORKS

RELATED APPLICATION

The present application is the national stage entry of International Patent Application No. PCT/US2018/033117 having a filing date of May 17, 2018, which claims priority to U.S. provisional application Ser. No. 62/515,716, filed on June 6, 2017, both of which are incorporated herein in their entirety by reference thereto.

FIELD OF THE INVENTION

The present invention relates to anatomical object detection in the field of medical imaging, and more particularly, to systems and methods for identifying and navigating anatomical objects using a visualization guide and/or haptic feedback.

BACKGROUND

Detection of anatomical objects using ultrasound imaging is an essential step for many medical procedures, such as regional anesthesia nerve blocks, and is becoming the standard in clinical practice to support diagnosis, patient stratification, therapy planning, intervention, and/or follow-up. As such, it is important that detection of anatomical objects and surrounding tissue occurs quickly and accurately.

Various systems based on traditional approaches exist for addressing the problem of anatomical detection and tracking in medical images, such as computed tomography (CT), magnetic resonance (MR), ultrasound, and fluoroscopic images. However, navigation to the target anatomical object and detection thereof requires high training skills, years of experience, and a sound knowledge of the body anatomy.

As such, a system and method that can efficiently guide the operators, nurses, medical students, and/or practitioners to find the target anatomical object would be welcomed in the art. Accordingly, the present disclosure is directed to a system and method for identifying and navigating anatomical objects using a visualization guide and/or haptic feedback.

SUMMARY OF THE INVENTION

Objects and advantages of the invention will be set forth in part in the following description, or may be obvious from the description, or may be learned through practice of the invention.

In one aspect, the present invention is directed to a method for scanning, identifying, and navigating at least one anatomical object of a patient via an imaging system. The method includes scanning the anatomical object via a probe of the imaging system, identifying the anatomical object via the probe, and navigating the anatomical object via the probe. Further, the method includes collecting data relating to operation of the probe during the scanning, identifying, and navigating steps. Moreover, the method includes inputting the collected data into a deep learning network configured to learn the scanning, identifying, and navigating steps relating to the anatomical object. In addition, the method includes generating a probe visualization guide for an operator based on the deep learning network. Thus, the method also includes displaying the probe visualization guide to the operator via a user display of the imaging system, wherein the probe visualization guide instructs the operator how to maneuver the probe so as to locate the anatomical object.

In one embodiment, the step of collecting data relating to the anatomical object during the scanning, identifying, and navigating steps may include generating at least one of one or more images or a video of the anatomical object from the scanning step and storing the one or more images or the video in a memory device. In another embodiment, the step of collecting data relating to the anatomical object during the scanning, identifying, and navigating steps may include monitoring at least one of movement or applied pressure of the probe via one or more sensors during at least one of the scanning, identifying, and navigating steps and storing data collected during monitoring in the memory device.

In further embodiments, the step of monitoring at least one of movement or applied pressure of the probe via one or more sensors may include monitoring a tilt angle of the probe during at least one of the scanning, identifying, and navigating steps. In several embodiments, the generating step and the monitoring step may be performed simultaneously.

In additional embodiments, the method may include determining an error between the one or more images or the video and the monitored movement of the probe. In such embodiments, the method may also include optimizing the deep learning network based on the error.

In particular embodiments, the probe visualization guide may include directions for moving the probe and/or a tilt angle for holding the probe during operation. In further embodiments, the method may include generating haptic feedback based on the deep learning network and sending the haptic feedback to probe of the imaging system.

In certain embodiments, the deep learning network may include one of one or more convolutional neural networks and/or one or more recurrent neural networks. Further, in several embodiments, the method may include training the deep learning network to automatically learn the scanning, identifying, and navigating steps relating to the anatomical object.

In another aspect, the present invention is directed to a method for analyzing at least one anatomical object of a patient via an imaging system. The method includes analyzing the anatomical object via a probe of the imaging system. Further, the method includes collecting data relating to operation of the probe during the analyzing step. The method also includes inputting the collected data into a deep learning network configured to learn the analyzing step relating to the anatomical object. Moreover, the method includes generating a probe visualization guide for an operator based on the deep learning network and displaying the probe visualization guide to the operator via a user display of the imaging system. Thus, the probe visualization guide instructs the operator how to maneuver the probe during operation thereof so as to locate the anatomical object. It should also be understood that the method may further include any of the additional steps and/or features as described herein.

In yet another aspect, the present invention is directed to an ultrasound imaging system. The imaging system includes a user display configured to display an image of an anatomical object, an ultrasound probe, and a controller communicatively coupled to the ultrasound probe and the user display. The controller includes one or more processors configured to perform one or more operations, including but not limited to analyzing the anatomical object via the ultrasound probe, collecting data relating to operation of the ultrasound probe the analyzing step, inputting the collected data into a deep learning network configured to learn the analyzing step relating to the anatomical object, generating a probe visualization guide for an operator based on the deep learning network, and displaying the probe visualization guide to the operator via the user display. Thus, the probe visualization guide is configured to instruct the operator how to maneuver the ultrasound probe during operation thereof so as to locate the anatomical object. It should also be understood that the imaging system may further include any of the additional steps and/or features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 1:
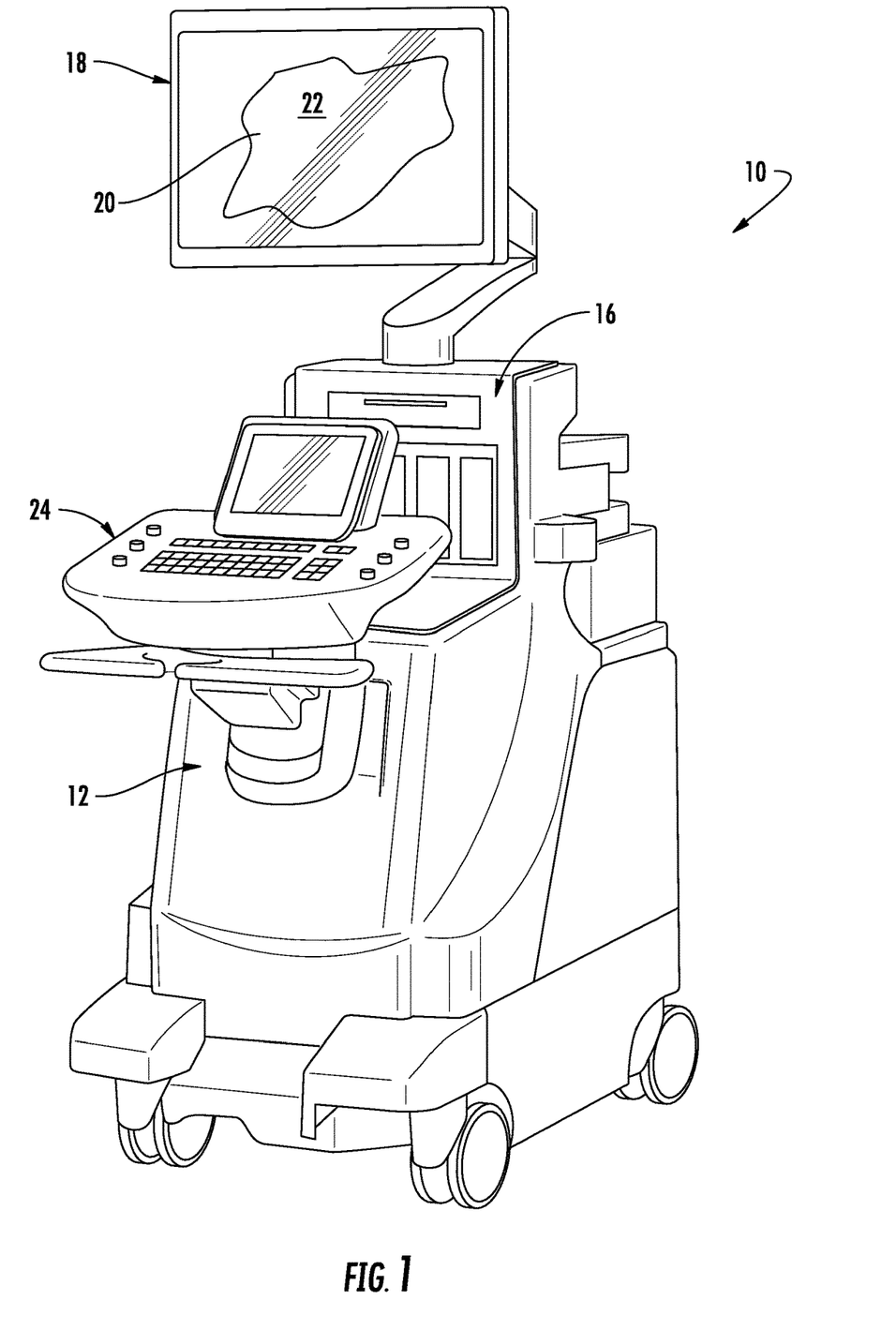
FIG. 1 illustrates a perspective view of one embodiment of an imaging system according to the present disclosure.
Figure 2:
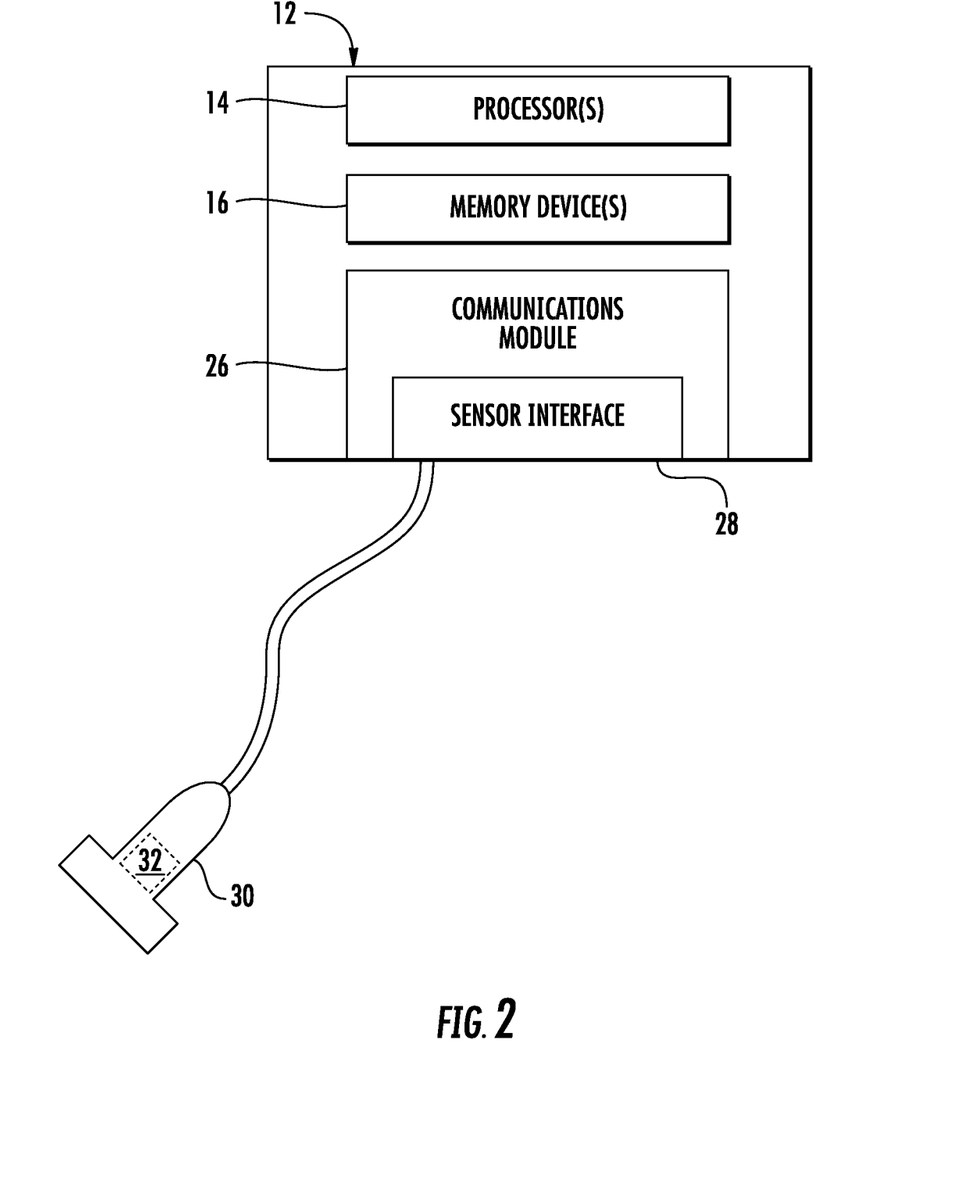
FIG. 2 illustrates a block diagram one of embodiment of a controller of an imaging system according to the present disclosure.

Referring now to the drawings, FIGS. 1 and 2 illustrate an imaging system 10 for scanning, identifying, and navigating anatomical objects of a patient according to the present disclosure. More specifically, as shown, the imaging system 10 may correspond to an ultrasound imaging system or any other suitable imaging system that can benefit from the present technology. Thus, as shown, the imaging system 10 generally includes a controller 12 having one or more processor(s) 14 and associated memory device(s) 16 configured to perform a variety of computer-implemented functions (e.g., performing the methods and the like and storing relevant data as disclosed herein), as well as a user display 18 configured to display an image 20 of an anatomical object 22 to an operator. In addition, the imaging system 10 may include a user interface 24, such as a computer and/or keyboard, configured to assist a user in generating and/or manipulating the user display 18.

Additionally, as shown in FIG. 2, the processor(s) 14 may also include a communications module 26 to facilitate communications between the processor(s) 14 and the various components of the imaging system 10, e.g. any of the components of FIG. 1. Further, the communications module 26 may include a sensor interface 28 (e.g., one or more analog-to-digital converters) to permit signals transmitted from one or more probes (e.g. the ultrasound probe 30) to be converted into signals that can be understood and processed by the processor(s) 14. It should be appreciated that the ultrasound probe 30 may be communicatively coupled to the communications module 26 using any suitable means. For example, as shown in FIG. 2, the ultrasound probe 30 may be coupled to the sensor interface 28 via a wired connection. However, in other embodiments, the ultrasound probe 30 may be coupled to the sensor interface 28 via a wireless connection, such as by using any suitable wireless communications protocol known in the art. As such, the processor(s) 14 may be configured to receive one or more signals from the ultrasound probe 30.

As used herein, the term "processor" refers not only to integrated circuits referred to in the art as being included in a computer, but also refers to a controller, a microcontroller, a microcomputer, a programmable logic controller (PLC), an application specific integrated circuit, a field-programmable gate array (FPGA), and other programmable circuits. The processor(s) 14 is also configured to compute advanced control algorithms and communicate to a variety of Ethernet or serial-based protocols (Modbus, OPC, CAN, etc.). Furthermore, in certain embodiments, the processor(s) 14 may communicate with a server through the Internet for cloud computing in order to reduce the computation time and burden on the local device. Additionally, the memory device(s) 16 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 16 may generally be configured to store suitable computer-readable instructions that, when implemented by the processor(s) 14, configure the processor(s) 14 to perform the various functions as described herein.

Figure 3:
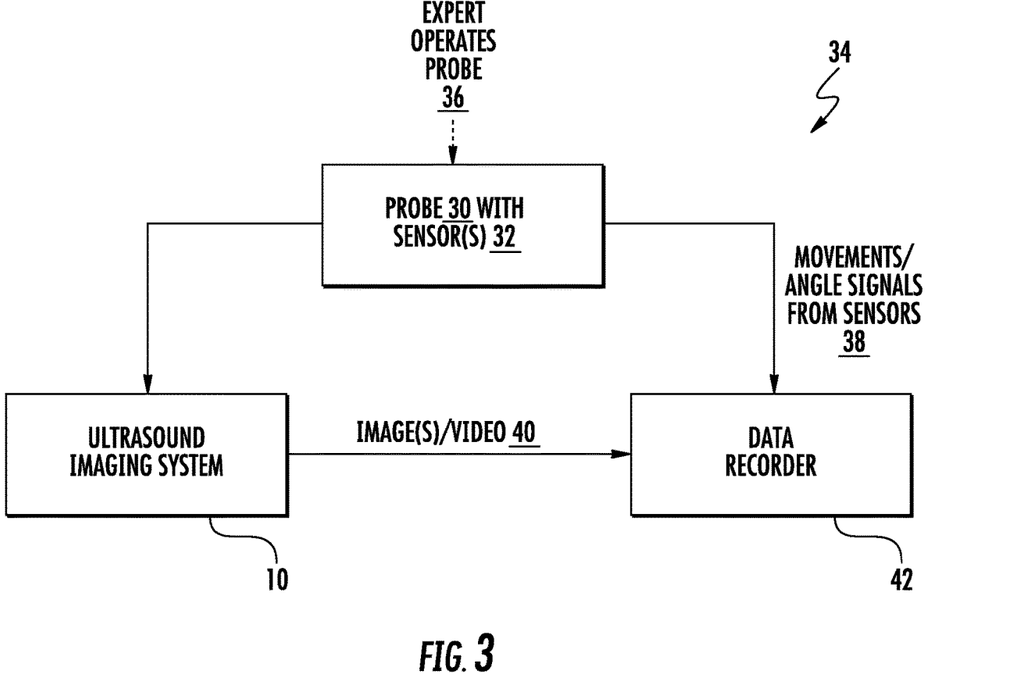
FIG. 3 illustrates a schematic block diagram of one embodiment of a data collection system for collecting images and/or videos together with movement and angles of a probe of an imaging system according to the present disclosure.
Figure 4:
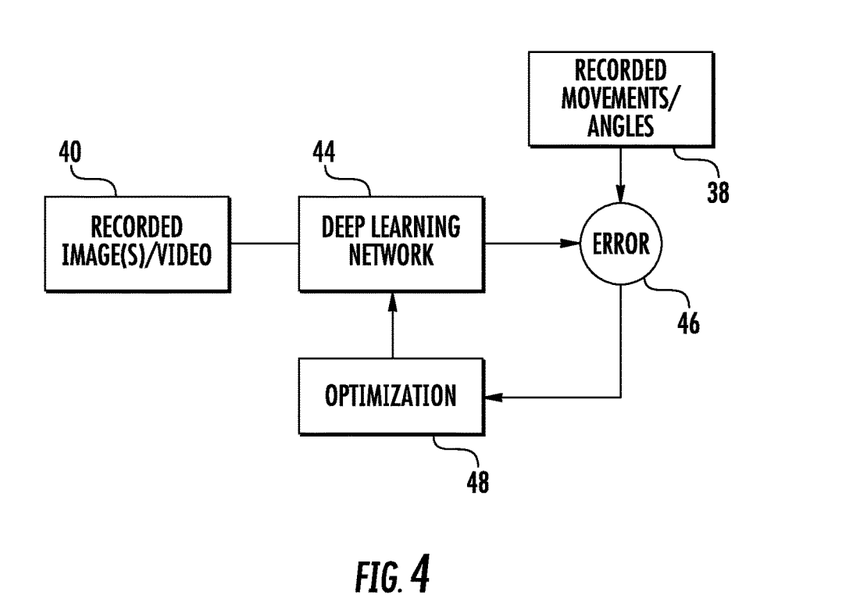
FIG. 4 illustrates a schematic block diagram of one embodiment of training a deep learning network based on the data collection system according to the present disclosure.
Figure 5:
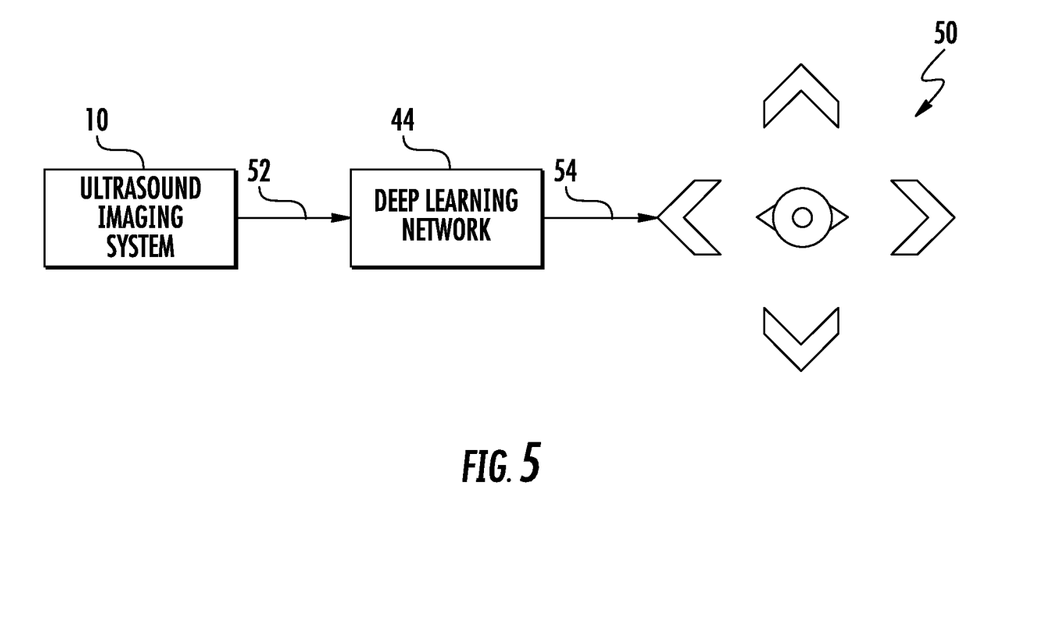
FIG. 5 illustrates a schematic block diagram of one embodiment of the system according to the present disclosure, particularly illustrating the deployed system generating a visualization guide for an operator during a scanning session.

Referring now to FIGS. 3-5, various schematic block diagrams of one embodiment of a system for scanning, identifying, and navigating anatomical objects 22 of a patient via an imaging system 10 are illustrated. As used herein, the anatomical object(s) 22 and surrounding tissue may include any anatomy structure and/or surrounding tissue of the anatomy structure of a patient. For example, in one embodiment, the anatomical object(s) 22 may include an interscalene brachial plexus of the patient, which generally corresponds to the network of nerves running from the spine, formed by the anterior rami of the lower four cervical nerves and first thoracic nerve. As such, the brachial plexus passes through the cervicoaxillary canal in the neck, over the first rib, and into the axilla (i.e. the armpit region), where it innervates the upper limbs and some neck and shoulder muscles. As such, the surrounding tissue of the brachial plexus generally corresponds to the sternocleidomastoid muscle, the middle scalene muscle, the anterior scalene muscle, and/or similar.

It should be understood, however, that the system and method of the present disclosure may be further used for any variety of medical procedures involving any anatomy structure in addition to those relating to the brachial plexus. For example, the anatomical object(s) 22 may include upper and lower extremities, as well as compartment blocks. More specifically, in such embodiments, the anatomical object(s) 22 of the upper extremities may include interscalene muscle, supraclavicular muscle, infraclavicular muscle, and/or axillary muscle nerve blocks, which all block the brachial plexus (a bundle of nerves to the upper extremity), but at different locations. Further, the anatomical object(s) 22 of the lower extremities may include the lumbar plexus, the fascia Iliac, the femoral nerve, the sciatic nerve, the abductor canal, the popliteal, the saphenous (ankle), and/or similar. In addition, the anatomical object(s) 22 of the compartment blocks may include the intercostal space, transversus abdominus plane, and thoracic paravertebral space, and/or similar.

Referring particularly to FIG. 3, a schematic block diagram of one embodiment of a data collection system 34 of the imaging system 10 for collecting images and/or videos 44 together with movement and angles 42 of the ultrasound probe 30 according to the present disclosure is illustrated. In other words, in certain embodiments, the images/videos 44 may be generated by the imaging system 10 and the movement of the probe 30 may be monitored simultaneously. More specifically, in several embodiments, as shown at 36, an expert (such as a doctor or ultrasound technician) scans the anatomical object 22 of the patient via the ultrasound probe 30 and identifies the anatomical object 22 via the user display 18. Further, the expert navigates the anatomical object 22 via the ultrasound probe 30 during the medical procedure. During scanning, identifying, and/or navigating the anatomical object 22, as shown at 40, the data collection system 34 collects data relating to operation of the probe 30 via one or more sensors 32, e.g. that may be mounted to or otherwise configured with the probe 30. For example, in one embodiment, the sensors 32 may include accelerometers or any other suitable measurement devices. More specifically, as shown at 38, the data collection system 34 is configured to monitor movements, including e.g. tilt angles, of the probe 30 via the sensors 32 during operation thereof and store such data in a data recorder 42. In additional embodiments, the imaging system 10 may also collect information regarding a pressure of the probe 30 being applied to the patient during scanning by the expert. Such information can be stored in the data recorder 42 for later use. Further, the ultrasound imaging system 10 may also store one or more images and/or videos (as shown at 40) of the probe 30 being operated by the expert in the data recorder 42.

Referring now to FIG. 4, a schematic block diagram of one embodiment of training a deep learning network 44 based on the data collected by the data collection system 34 of FIG. 3 according to the present disclosure is illustrated. Further, in several embodiments, the imaging system 10 is configured to train the deep learning network 44 to automatically learn the scanning, identifying, and navigating steps relating to operation of the probe 30 and the anatomical object(s) 22. In one embodiment, the deep learning network 44 may be trained once offline. More specifically, as shown in the illustrated embodiment, the imaging system 10 inputs the collected data into the deep learning network 44, which is configured to learn the scanning, identifying, and navigating steps relating to operation of the probe 30 and the anatomical object(s) 22. Further, as shown, the recorded image(s) and/or videos 38 may be input into the deep learning network 44. As used herein, the deep learning network 44 may include one or more deep convolutional neural networks (CNNs), one or more recurrent neural networks, or any other suitable neural network configurations. In machine learning, deep convolutional neural networks generally refer to a type of feed-forward artificial neural network in which the connectivity pattern between its neurons is inspired by the organization of the animal visual cortex, whose individual neurons are arranged in such a way that they respond to overlapping regions tiling the visual field. In contrast, recurrent neural networks (RNNs) generally refer to a class of artificial neural networks where connections between units form a directed cycle. Such connections create an internal state of the network which allows the network to exhibit dynamic temporal behavior. Unlike feed-forward neural networks (such as convolutional neural networks), RNNs can use their internal memory to process arbitrary sequences of inputs. As such, RNNs can extract the correlation between the image frames in order to better identify and track anatomical objects in real time.

Still referring to FIG. 4, the imaging system 10 may also be configured to determine an error 46 between the image(s)/video(s) 40 and the monitored movement 38 of the probe 30. In such embodiments, as shown at 48, the imaging system 10 may further include optimizing the deep learning network 44 based on the error 46. More specifically, in certain embodiments, the processor(s) 14 may be configured to optimize a cost function to minimize the error 46. For example, in one embodiment, the step of optimizing the cost function to minimize the error 46 may include utilizing a stochastic approximation, such as a stochastic gradient descent (SGD) algorithm, that iteratively processes portions of the collected data and adjusts one or more parameters of the deep neural network 48 based on the error 46. As used herein, a stochastic gradient descent generally refers to a stochastic approximation of the gradient descent optimization method for minimizing an objective function that is written as a sum of differentiable functions. More specifically, in one embodiment, the processor(s) 14 may be configured to implement supervised learning to minimize the error 46. As used herein, "supervised learning" generally refers to the machine learning task of inferring a function from labeled training data.

Once the deep learning network 44 is trained, as shown in FIG. 5, the controller 12 of the imaging system 10 is configured to deploy a probe visualization guide 50 to an operator based on the deep learning network 44, e.g. during a subsequent scanning session. For example, in particular embodiments, the probe visualization guide 50 may include directions for moving the probe 30 and/or tilt angle(s) for holding the probe 30 during the scanning session. As such, the operator can easily and quickly maneuver the probe 50 to find the desired anatomical object 22 of the patient since the deep learning network 44 is trained to do so. More specifically, as shown, the collected data from the imaging system 10 is used an input 52 to the deep learning network 44. Further, as shown, the deep learning network 44 then generates a network output 54 that is used to generate the probe visualization guide 50 for the operator based on the deep learning network 44. Further, as shown in the illustrated embodiment, the probe visualization guide 50 may be displayed to the operator via the user display 18 of the imaging system 10. Thus, the probe visualization guide 50 is configured to instruct the operator how to maneuver the ultrasound probe 30 during operation thereof so as to locate the anatomical object 22.

Figure 6:
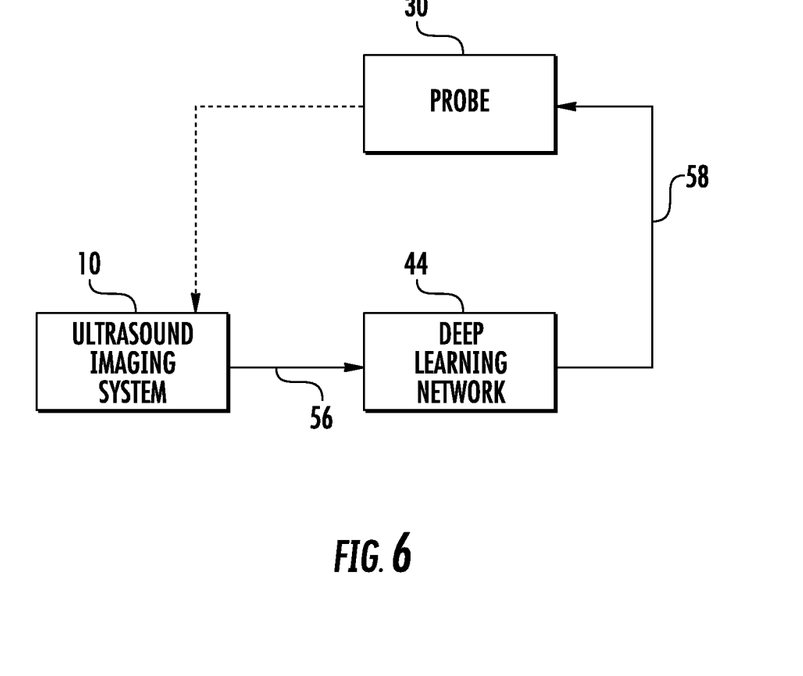
FIG. 6 illustrates a schematic block diagram of one embodiment of the system according to the present disclosure, particularly illustrating the deployed system generating haptic feedback for the probe during a scanning session.

Referring now to FIG. 6, in further embodiments, the collected data from the imaging system 10 may be used an input 56 to the deep learning network 44. Further, as shown, the deep learning network 44 may then generate haptic feedback 58 based on the deep learning network 44. As described herein, haptic feedback generally refers to feedback that uses the sense of touch in a user interface design to provide information to an end user. For example, examples of haptic feedback may include vibration, resistive forces, motions, or similar. Thus, as shown, the haptic feedback 58 may be sent to the probe 30 of the imaging system 10. Accordingly, the haptic feedback 58 of the probe 30 is configured to guide the operator in locating the anatomical object 22 of the patient.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for scanning, identifying, and navigating to at least one anatomical object of a patient via an imaging system, wherein the imaging system comprises a controller for performing the method comprising:
   scanning, identifying, and navigating to the at least one anatomical object via an ultrasound probe during manual operation of the probe;
   monitoring at least one of movement or applied pressure of the probe via one or more sensors during at least one of the scanning, identifying, and navigating to the at least one anatomical object;
   collecting data relating to the scanning, identifying, and navigating to the at least one anatomical object during the manual operation of the probe;
   receiving, via a deep learning network, the collected data relating to the manual operation of the ultrasound probe, the deep learning network configured to learn the scanning, identifying, and navigating the at least one anatomical object, wherein the deep learning network comprises at least one of one or more convolutional neural networks or one or more recurrent neural networks;
   training the deep learning network to automatically learn the scanning, identifying, and navigating to the at least one anatomical object;
   generating, via the deep learning network, a probe visualization guide based on the learned at least one anatomical object from the collected data;
   and displaying the probe visualization guide via a user display of the imaging system, wherein the probe visualization guide provides instructions on how to maneuver the probe so as to locate the at least one anatomical object, and wherein the probe visualization guide generated by the deep learning network comprises at least one of one or more directions for moving the probe or a tilt angle for holding the probe.

2. The method of claim 1, wherein collecting data relating to the manual operation of the probe during the scanning, identifying, and navigating to the at least one anatomical object further comprises:
   producing at least one of one or more images or a video of the at least one anatomical object from the scanning step; and
   storing the one or more images or the video in a memory device.

3. The method of claim 2, further comprising
   storing data collected during the monitoring in the memory device.

4. The method of claim 1, wherein monitoring at least one of the movement or the applied pressure of the probe via one or more sensors further comprises monitoring a tilt angle of the probe during at least one of the scanning, identifying, and navigating to the at least one anatomical object.

5. The method of claim 1, wherein the generating step and the monitoring step are performed simultaneously.

6. The method of claim 1, further comprising determining an error between the one or more images or the video and the monitored movement of the probe.

7. The method of claim 6, further comprising optimizing the deep learning network based on the error.

8. The method of claim 1, further comprising generating haptic feedback based on the deep learning network and sending the haptic feedback to probe of the imaging system.

9. A method for analyzing at least one anatomical object of a patient via an imaging system, wherein the imaging system comprises a controller for performing the method comprising:
   analyzing the at least one anatomical object via scanning, identifying, and navigating to the at least one anatomical object during manual operation of an ultrasound probe of the imaging system;
   monitoring at least one of movement or applied pressure of the probe via one or more sensors during the analyzing of the at least one anatomical object;
   collecting data relating to the scanning, identifying, and navigating to the at least one anatomical object during the manual operation of the probe during the analyzing step;
   receiving, via a deep learning network, the collected data relating to the manual operation of the ultrasound probe, the deep learning network configured to learn the scanning, identifying, and navigating to the at least one anatomical object using the analyzing step, wherein the deep learning network comprises at least one of one or more convolutional neural networks or one or more recurrent neural networks;
   training the deep learning network to automatically learn the scanning, identifying, and navigating to the at least one anatomical object;
   generating, via the deep learning network, a probe visualization guide based on the learned at least one anatomical object from the collected data;
   and displaying the probe visualization guide to a first operator via a user display of the imaging system, wherein the probe visualization guide provides instructions on how to maneuver the probe so as to locate the at least one anatomical object, and wherein the probe visualization guide generated by the deep learning network comprises at least one of one or more directions for moving the probe or a tilt angle for holding the probe.

10. An ultrasound imaging system, comprising:
a user display configured to display an image of the at least one anatomical object;
an ultrasound probe;
a controller communicatively coupled to the ultrasound probe and the user display, the controller comprising one or more processors configured to perform one or more operations, the one or more operations comprising:
analyzing the at least one anatomical object via scanning, identifying, and navigating to the at least one anatomical object during manual operation of the ultrasound probe;
monitoring at least one of movement or applied pressure of the probe via one or more sensors during the analyzing of the at least one anatomical object;
collecting data relating to the scanning, identifying, and navigating to the at least one anatomical object during the manual operation of the ultrasound probe during the analyzing step;
receiving, via a deep learning network, the collected data relating to the manual operation of the ultrasound probe, the deep learning network configured to learn the scanning, identifying, and navigating to the at least one anatomical object using the analyzing step, wherein the deep learning network comprises at least one of one or more convolutional neural networks or one or more recurrent neural networks;
training the deep learning network to automatically learn the scanning, identifying, and navigating to the at least one anatomical object, generating, via the deep learning network, a probe visualization guide based on the learned at least one anatomical object from the collected data;
and displaying the probe visualization guide to the first operator via the user display, wherein the probe visualization guide provides instructions on how to maneuver the ultrasound probe so as to locate the at least one anatomical object, and wherein the probe visualization guide generated by the deep learning network comprises at least one of one or more directions for moving the probe or a tilt angle for holding the probe.

11. The imaging system of claim 10, wherein collecting data relating to the manual operation of the ultrasound probe further comprises:
generating at least one of one or more images or a video of the at least one anatomical object; and
storing the one or more images or the video in a memory device of the ultrasound imaging system.

12. The imaging system of claim 10, wherein the one or more operations further comprise monitoring the tilt angle of the probe.

13. The imaging system of claim 10, wherein the one or more operations further comprise determining an error between the one or more images or the video and the monitored movement of the ultrasound probe.

14. The imaging system of claim 10, further comprising the controller configured to generate haptic feedback based on the deep learning network and send the haptic feedback to ultrasound probe of the imaging system.

* * * * *